United States Patent [19]
Veith et al.

[11] Patent Number: 5,356,364
[45] Date of Patent: Oct. 18, 1994

[54] METHOD FOR EMBOSSING WEBS

[75] Inventors: Jerome S. Veith, Menasha; Edward H. Grupe; Joseph W. Brown, both of Appleton, all of Wis.

[73] Assignee: Kimberly-Clark Corporation, Neenah, Wis.

[21] Appl. No.: 870,528

[22] Filed: Apr. 17, 1992

Related U.S. Application Data

[63] Continuation-in-part of Ser. No. 660,317, Feb. 22, 1991, abandoned.

[51] Int. Cl.⁵ .................. B65H 45/12; B31F 1/07
[52] U.S. Cl. ..................... 493/395; 72/196; 101/23; 101/6; 101/32
[58] Field of Search .......... 493/395, 402, 403; 264/282, 284; 101/5, 6, 22, 23, 24, 32, 376; 100/211; 72/191, 196, 385

[56] References Cited

U.S. PATENT DOCUMENTS

| | | | |
|---|---|---|---|
| 2,257,428 | 9/1941 | Ruegenberg | 154/55 |
| 3,314,339 | 4/1967 | Guffy | 493/403 |
| 3,717,532 | 2/1973 | Kamp | 156/199 |
| 3,911,187 | 10/1975 | Raley | 264/284 |
| 4,361,085 | 11/1982 | Schutz | 493/395 |
| 4,498,390 | 2/1985 | Bowling | 101/6 |
| 4,913,911 | 4/1990 | Wildt | 264/284 |

FOREIGN PATENT DOCUMENTS

| | | | |
|---|---|---|---|
| 0338792 | 10/1989 | European Pat. Off. | B31F 1/07 |
| 0498623 | 8/1992 | European Pat. Off. | B31F 1/07 |
| 0499942 | 8/1992 | European Pat. Off. | B31F 1/07 |

*Primary Examiner*—Jack Lavinder
*Attorney, Agent, or Firm*—Gregory E. Croft

[57] ABSTRACT

Embossing a web between unmatched male and female embossing elements, wherein the sidewall slope of the female element is different than the sidewall slope of the male element, provides an embossed web having markedly improved embossing pattern definition and, in the case of roll products, greater roll bulk at equivalent roll firmness. The unmatched male and female embossing elements are preferably made by laser engraving rubber embossing rolls.

13 Claims, 7 Drawing Sheets

METHOD FOR EMBOSSING WEBS

This application is a continuation-in-part of copending U.S. patent application Ser. No. 07/660,317 filed Feb. 22, 1991, now abandoned.

BACKGROUND OF THE INVENTION

In the manufacture of tissue products such as facial tissue, bath tissue and paper towels, it is known that embossing increases the bulk of the product as well as improves aesthetic appeal. A trade-off, however, is the fact that embossing also reduces the strength of the embossed sheet and, in the case of roll products, an increase in bulk is accompanied by a decrease in roll firmness.

SUMMARY OF THE INVENTION

It has now been discovered that male and female embossing elements having different geometries (unmatched embossing elements) and which are preferably made of a relatively deformable material such as rubber or plastic can produce a visually more distinct embossing pattern which imparts greater bulk to the embossed sheet with substantially less loss of firmness compared to conventional embossing techniques. Such differences in geometry create "pinch points" as the male and female embossing elements are engaged where the web to be embossed is compressed or pinched between a sidewall of the female embossing element and a bottom corner of the male embossing element and/or is compressed between a sidewall of the male embossing element and the top edge of the female embossing element. It is believed that the pinch points cause isolated compressions of the web which impart durability to the embossments. This results in embossments which are more distinct than conventional embossments and provides greater bulk at a given level of firmness. For purposes herein, embossing elements are protrusions (male embossing elements) or depressions (female embossing elements) formed on the surface of a roll or plate used for creating corresponding deflections (embossments) in a web. Common methods of forming embossing elements include engraving or etching.

Hence in one aspect, the invention resides in a method for embossing a web comprising deflecting the web between unmatched male and female embossing elements, wherein the slope of at least one sidewall of the female embossing elements is different than the slope of the corresponding sidewall of the male embossing elements.

In another aspect, the invention resides in a pair of embossing rolls having unmatched male and female embossing elements, wherein the slope of at least one sidewall of the female embossing elements is different than the slope of the corresponding sidewall of the male elements. The pair of embossing rolls can include one roll having all male elements and the second roll having all female elements, or each roll can have both male and female elements. Preferably at least one of the embossing rolls, and most preferably both of the embossing rolls, is covered with a rubber surface. Rubber embossing elements yield slightly to the web and are believed to be less likely to damage the strength of the web during embossing.

In a further aspect, the invention resides in an embossed web produced by the methods described herein.

More particularly, the invention resides in a creped bath or toilet tissue having a sheet bulk/embossed area ratio of about 50 or greater, more preferably about 60 or greater, and most preferably about 75 or greater, wherein sheet bulk is expressed as cubic centimeters per gram and embossed area is expressed as the fraction of the surface area which has been deflected inwardly from the outside of the tissue web. Preferably, such bath tissues have a sheet bulk of about 12 cubic centimeters per gram or greater, more preferably about 13 or 14 cubic centimeters per gram or greater.

Sheet bulk is measured substantially in accordance with TAPPI Standard T411-68 except for the loading on the pressure foot, which is 95 grams per square inch. The method utilizes a TMI Bench Micrometer, Model 549MSP having a 2 inches diameter anvil, and comprises placing a single sheet of tissue on the anvil such that all points on the peripheries of the contact surfaces are at least ¼ inch in from the edges of the sample. The instrument motor is started and two measurements are taken within 6 inches of each other in the cross-machine direction of the sample. A reading is taken near the end of the dwell time on each test and is read to the nearest scale division. The average of the two readings is the sheet bulk of the tissue.

The embossed area of the tissue is determined by simply filling in the embossing depressions in the tissue with a black pen and using standard image analysis practices to measure the percent area of the tissue which has been darkened with the pen. More particularly, one sheet of bathroom tissue is removed from the roll and placed on a table with the tissue surface from the outside of the roll facing up. All of the embossing depressions or channels of the tissue sheet are darkened using a BIC ® Micro Metal black ink pen. Care should be taken to only darken in the indented portions of the sample as accurately as possible. The marked tissue sheet is then subjected to image analysis by placing the tissue sheet on a uniformly well lighted table. A camera (Dage MTI CCD Video Camera-Model #VE CCD) and lens assembly (Nikkon 28-85 mm zoom) are mounted on an adjustable overhead stand with the camera lens pointed downward at the sample. The tissue is brought into focus so that the entire screen is filled with the embossed sample to be examined. The image is acquired into an image analysis system (Sun Spark Station 1 with PGT Imex System Feature Analysis Software) and a detection threshold is set. The image is binarized and the field is examined for total embossed (black) area, which is expressed as a decimal fraction between 0 and 1.

As indicated above, a feature of this invention pertains to the requirement that the male and female embossing elements are "unmatched". As used herein, this term is intended to mean that the male and female embossing elements are not identical in shape, but still are positioned relative to each other in registry such that they engage. This is meant to distinguish from conventional "matched" steel embossing elements in which the male elements are engraved first and the female elements are subsequently made from the male elements, or vice versa, so that both elements are virtually inverse or reciprocal images of each other within the practicalities of manufacturing tolerances. This is not the case with the embossing elements of this invention, wherein although the male and female elements fit together or engage reasonably well, the sidewall slopes of the male and female embossing elements differ sufficiently to provide differential compression and/or shear on certain portions of the web when the embossing elements are engaged, meaning that all portions of the web which form an embossment sidewall are not compressed and/or sheared the same. This differential compression occurs when a sidewall of the male embossing element approaches contact with an upper corner of the female embossing element and/or a sidewall of the female embossing element approaches contact with a bottom corner of the male embossing element. Both conditions can occur simultaneously in the same male/female embossing element pair.

It is preferable that the slope of the male element sidewall be from about 5° to about 85°, and more preferably from about 50° to about 70° or greater. It is believed that steeper sidewall angles create a more permanent kink in the web in the vicinity where the embossment meets the undeflected area of the web when the slope of the male element sidewall is less than the slope of the female element sidewall. Because the depth of the resulting embossment is determined by the extent to which the male embossing element penetrates the female embossing element, in this embodiment of the invention the difference in sidewall slopes should not be so great that the penetration or degree of engagement of the male embossing element is insufficient to achieve the desired bulk. Although the degree of difference between the sidewall slope of the male and female elements can vary, it is preferred that the sidewall slope of the male element be at least about 2° greater or less than the corresponding slope of the female element, and more preferably from about 5° to about 10° greater or less than the corresponding slope of the female element. For purposes herein, the sidewall slope is measured relative to the plane of the undeflected web during embossing, with the maximum slope being perpendicular (90°) to the undeflected web. This is described in greater detail below with regard to FIG. 3.

It must be kept in mind that the practicalities of commercial engraving limit the ability to make embossing rolls in which the male and female embossing elements contact each other in the same manner everywhere on the embossing roll or plate. When viewing embossing element engagement in two dimensions (cross-sectional photographs), some embossing elements will be shown to contact each other on both sides as hereinafter illustrated in FIG. 3. In other instances, some embossing elements will be shown to contact each other only on one side. In still other areas, the embossing elements may appear to not touch at all. However, overall (over the entire embossed sheet surface) there are a sufficient and substantial number of pinch points to impart exceptional bulk and firmness to the web and integrity to the embossments. The varying degrees of engagement exhibited by the male and female embossing elements in accordance with this invention will be further illustrated and discussed in connection with FIG. 4.

When manufacturing embossing rolls for use in connection with this invention, laser engraving is a preferred method of manufacture because of its precision and lower cost. Laser engraved rubber sleeves for embossing rolls and laser engraved plates are commercially available from Midwest Rubber Plate Co., Menasha, Wis. The material of the male and female embossing elements is preferably a deformable material such as rubber, plastic or the like. Such materials are not only more forgiving with respect to degrading the strength of the web during embossing, but they also are suitable for laser engraving. As used herein, "rubber" is meant to include any relatively deformable material having a Shore A hardness of about 100 or less and preferably about 90 or less. Other suitable deformable materials include nylon, polyesters, polyurethane, polytetrafluoroethylene (Teflon), poly(vinylidene fluoride co hexafluoropropylene) (Viton), and the like.

Although deformable embossing element materials are preferred, it is also within the scope of certain aspects of this invention for the embossing elements to be steel or combinations of steel and rubber or other deformable materials. For example, the male elements can be steel and the female elements can be a deformable material, such as rubber, or vice versa. It will be appreciated that many different suitable combinations of materials are possible and within the scope of this invention. The steel rolls of this invention can also be used for bonding nonwovens by heating the rolls to provide a unique bonding pattern.

The web to be embossed in accordance with this invention can be any web suitable for embossing, including paper, tissue, nonwovens, films, laminates, combinations thereof and the like. The webs can be preheated or premoistened. In the case of tissue webs, which for purposes herein means webs intended for use as facial tissue, bath tissue, table napkins and paper towels, the web can be layered or nonlayered, creped or uncreped, wet pressed or throughdried, single-ply or two-ply or multiple ply, and can comprise natural and/or synthetic fibers. Creped tissue webs are preferred, which have a finished dry basis weight of from about 5 to about 40 pounds per 2880 square feet per ply and a geometric mean tensile strength of from about 300 to about 12,000 grams per 3 inches of width.

For purposes herein, roll bulk is the volume of a product (in cubic centimeters) divided by the weight of the product (in grams). For roll products such as bath tissue and paper towels which have a hollow core, the product volume "V" is calculated as follows:

$$V = \pi(R_1^2 - R_2^2)W$$

wherein $R_1$ = radius of the roll;
$R_2$ = outside radius of the hollow core; and
$W$ = width of the roll, For a rectangular stack of product such as facial tissue, the product volume is simply the length x height x width of the stack.

The Firmness Index is a measure of the distance, expressed in inches, that a weighted probe deflects the surface of a roll or stack of product, A greater deflection distance and hence a greater Firmness Index reflects lesser product firmness, The method and apparatus for measuring the Firmness Index will be described hereinafter in connection with the detailed description of FIGS. 7 and 8.

DETAILED DESCRIPTION OF THE INVENTION

Figure 1:
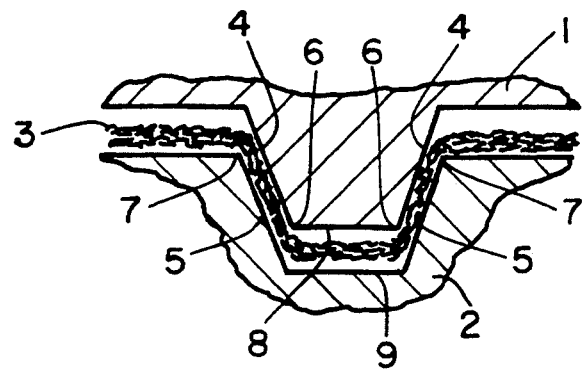
FIG. 1 is a schematic illustration of prior art embossing using matched steel embossing elements.

Referring to the drawing, the invention will be described in greater detail.

FIG. 1 illustrates an embossing process of the prior art in which a tissue web is embossed between matched steel embossing elements. Shown is a male steel embossing element 1 and a matching female steel embossing element 2 in an engaged position. The web 3 being embossed is deflected between the embossing elements as shown. The amount of web compression is greatest between the male embossing element sidewalls 4 and the female embossing element sidewalls 5. Because the sidewall slope of the matched steel male and female embossing elements is identical, the extent of web compression is substantially uniform at all points between the bottom edge 6 of the male element and the top edge 7 of the female element. Under typical embossing conditions, the web is relatively uncompressed in the region between the bottom 8 of the male element and the bottom 9 of the female element.

Figure 2:
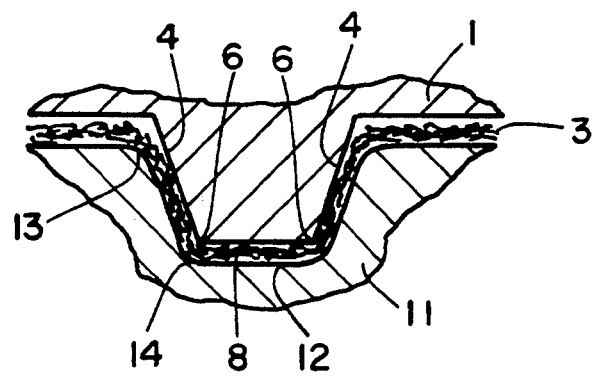
FIG. 2 is a schematic illustration of prior art embossing using steel embossing elements against a rubber roll.

FIG. 2 illustrates another embossing process of the prior art wherein a tissue web 3 is embossed between a male steel embossing element 1 and a rubber embossing surface 11 which partially conforms to the steel male element when engaged as shown. In this type of embossing process, the greatest degree of web compression occurs between the bottom 8 of the steel element and the corresponding surface 12 of the rubber. In the area of the male element sidewalls 4, there is a gradual increase in web compression from a point 13 on the undeflected surface of the rubber to a point 14 near the bottom edge 6 of the male element.

Figure 3A:
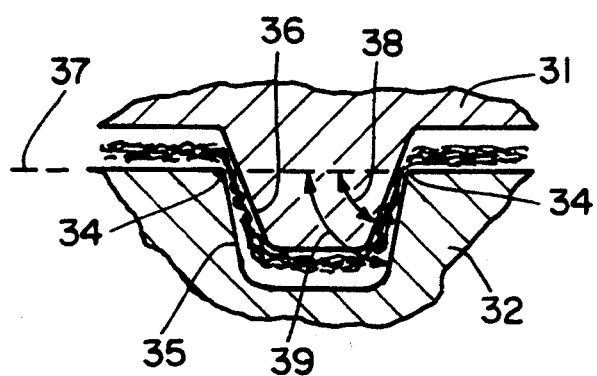
FIGS. 3A and 3B are schematic illustrations of an embossing method in accordance with this invention and the resulting embossed product.
Figure 3B:
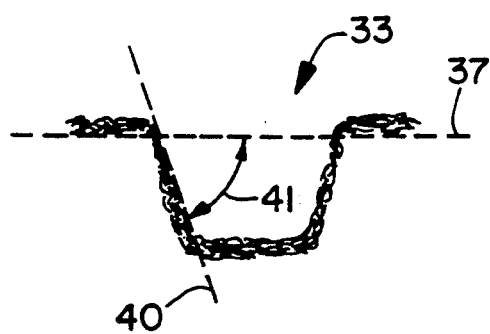

FIG. 3A illustrates a preferred embossing method of this invention in which a tissue web 3 is deflected between a male embossing element 31 and an unmatched female embossing element 32. FIG. 3B illustrates the resulting embossment 33 of the embossed product. Unlike the prior art embossing methods illustrated in FIGS. 1 and 2, the greatest degree of web compression and/or shear in the method of this embodiment of the invention occurs in the circled areas 34 located in the vicinity of the top edge of the female element. This occurs because in this embodiment the sidewall slope of the female element sidewall 35 is greater than the sidewall slope of the male element sidewall 36. It is theorized that applying maximum compression and/or shear only at the edge of the embossment realigns or deforms the fibers in this area in such a manner to give the resulting embossment greater structural integrity. In effect a more permanent crease or bend is imparted to the web at the edge of the embossment which results in greater embossment distinctness and a greater firmness retention for the embossed web. As previously described, the sidewall slopes are measured relative to the plane of the undeflected web as indicated by dashed line 37. The sidewall slope of the male embossing element as shown in FIG. 3A is indicated by the angle represented by the double arrow 38. The sidewall slope of the female embossing element is the angle represented by the double arrow 39. It is preferred that the male and female embossing elements are both made of rubber or other resilient material to provide an embossing surface which is more forgiving than steel and is less likely to cut the web at the point of near contact between the male and female embossing elements.

FIG. 3B also illustrates the maximum angle of deformation exhibited by the embossment 33. Shown is the undeflected plane of the web 37 and a line 40 which is aligned parallel with the centerline of the embossment sidewall to give the greatest value for the angle represented by the double arrow 41. Determination of the maximum angle of deformation can readily be done with the naked eye by using a representative cross-sectional photograph of the product.

However, the maximum angle of deflection can also be calculated using image analysis procedures. One method to accomplish this is to input the cross-sectional photograph into an image analyzer with the general center of the cross-section running in the horizontal, or x, direction. The computer image is corrected for shading differences and then is discriminated to create a binary image in which the tissue component is detected. Next, the binary image is manually edited to remove any gross smudges appearing in areas outside of the tissue component. A series of dilations is performed to fill in void areas of the tissue image. Then, an opposite set of erosions is performed to maintain the tissue sheet's contour. Finally, the resulting tissue image is skeletonized to a line of pixels. Precautions must be taken to preserve line endpoints during skeletonization. The image that results from this step is equivalent to a line drawn through the center of the tissue cross-section. Once the skeletonized image is obtained, it may be broken up into line segments. Typically, 32 line segments are created across the y-direction of the image. The angle of the individual line segments is easily measured as the inverse tangent of the ratio of Feret Y or Feret X. The maximum angle of the line segments is a measure of the steepness of the embossment sidewall.

Figure 4A:
FIGS. 4A, 4B, and 4C are cross-sectional photographs of a tissue web being embossed between male and female embossing elements in accordance with this invention, illustrating the varying degrees of contact between the male and female elements which can occur within the same embossing pattern.
Figure 4B:
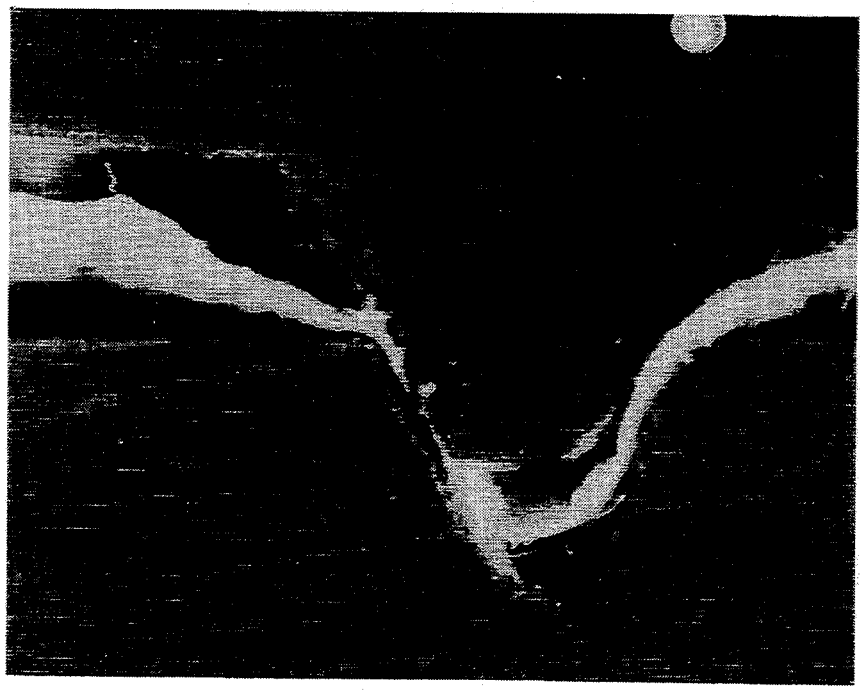
Figure 4C:
Figure 9:
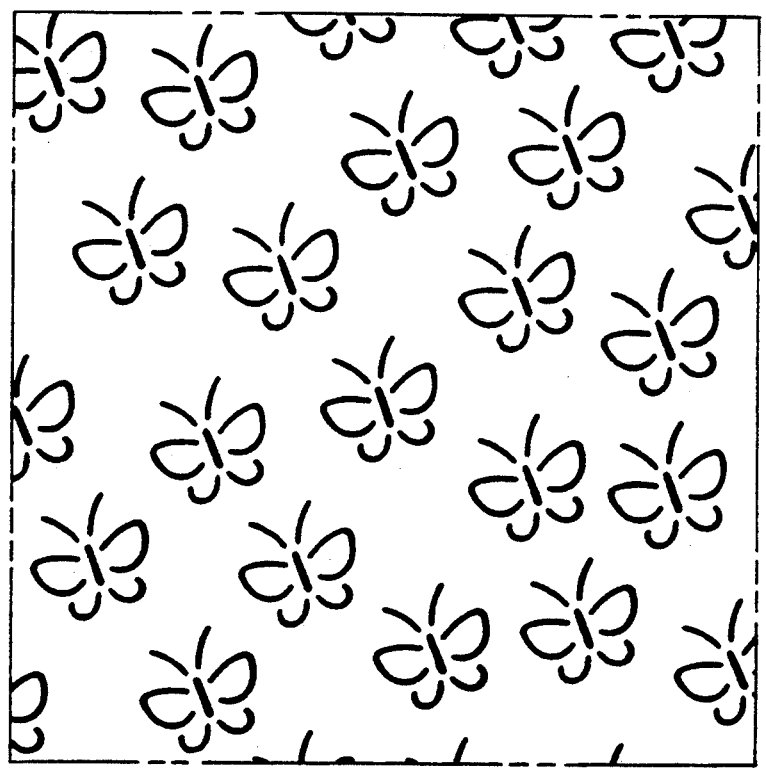
FIG. 9 represents the particular embossing pattern referred to in the description of the previous Figures.

FIGS. 4A, 4B and 4C are cross-sectional photographs (magnified 25×) of a creped tissue web being embossed between unmatched, laser engraved, rubber embossing elements in accordance with this invention. The embossing pattern was that as illustrated in FIG. 9. The cross-sections are taken at different positions of an embossing element to illustrate the manner in which the web is acted upon by the embossing elements in general and the variation in the manner in which the embossing elements engage. The particular embossing elements illustrated were from rubber sleeves adapted to be used on embossing rolls. The dimensions of the male embossing elements, in inches, were 0.060 in depth, 0.085 wide at the top, and 0.025 wide at the bottom. The sidewall slope of the male embossing elements was about 60°.

The dimensions of the female elements, also in inches, were 0.050 in depth, 0.055 wide at the top, and about 0.015 wide at the bottom, which was rounded. The sidewall slope of the female embossing elements was about 65°. As the photographs clearly show, the effect of using unmatched embossing elements has a variable effect on the web on a micro scale. However, a common effect is the compression or shear of the web at some point along the sidewall of the male embossing element where it approaches contact with the sidewall of the female embossing element. The differing sidewall slopes of the two elements prevent complete engagement and cause the web to be pinched off at some point while being virtually uncompressed at bottom of the male element. For this to occur consistently it is preferred that the maximum width of the male embossing element be at least as great as the maximum width of the female embossing element. Although not shown in these photographs, the relative positions of any given male and female embossing elements also change with time as the embossing elements of the two rolls or sleeves rotate in and out of engagement. Hence, in FIG. 4A for example, there apparently was initial contact between the male and female embossing elements on the left side prior to the photograph being taken (note the compression of the web at the top of the female embossing element left sidewall). Hence, when interpreting these photographs, one must not only take into account the imperfections of the laser engraving process, but also the dynamics (rolling action) of the embossing process.

Figure 5A:
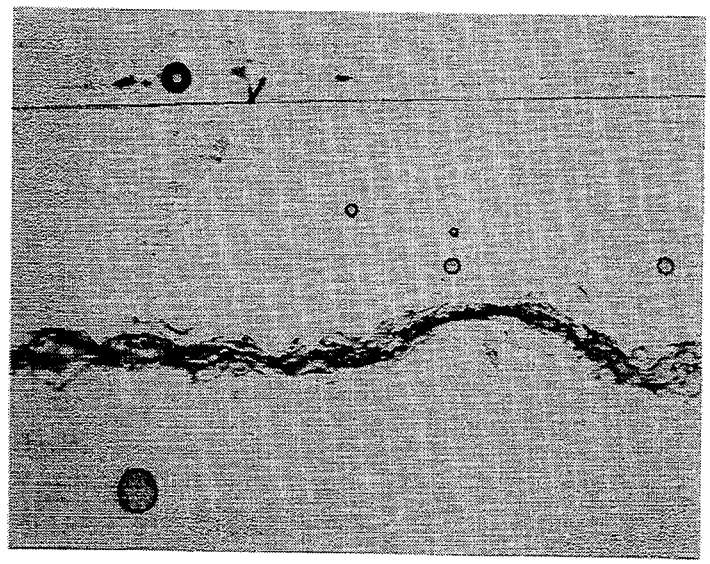
FIGS. 5A and 5B are cross-sectional photographs comparing a conventional embossed tissue web and a web in accordance with this invention, respectively.
Figure 5B:
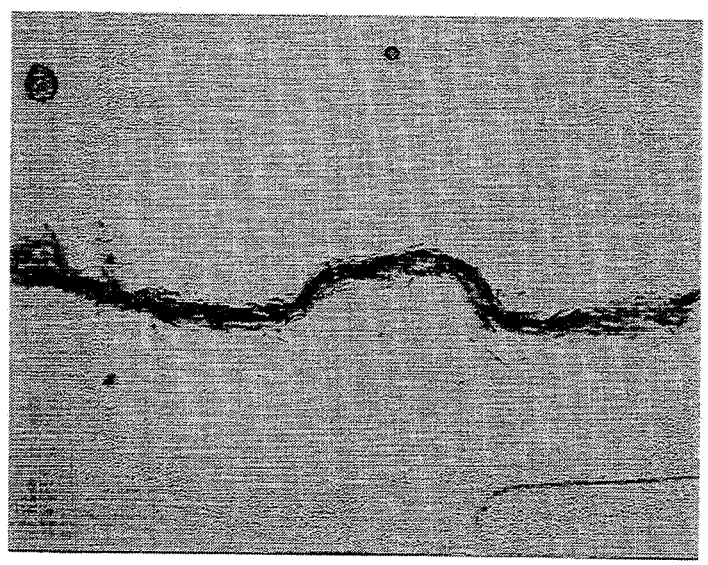

FIGS. 5A and 5B are cross-sectional photographs (magnified 20×) of a conventional embossed product and a product in accordance with this invention, respectively, using the embossing pattern illustrated in FIG. 9. Shown in FIG. 5A is a conventional single ply embossed creped tissue which has been embossed between a steel roll and a rubber roll. FIG. 5B shows a like web embossed using laser engraved rubber rolls having unmatched male and female embossing elements in accordance with this invention. Note the greater distinctness of the embossment in FIG. 5B due to the more sharply angled sidewalls. Also note the relative thickness of the two webs in the area of the edge of the embossments. In the web of FIG. 5B, this area is significantly thinner than the other areas along the sidewalls of the embossment. In contrast, the corresponding areas of the conventional embossment of FIG. 5A are no thinner than the other areas along the embossment sidewalls. This occurs throughout the entire web. It is theorized that applying maximum compression and/or shear only at the edge of the embossment realigns or deforms the fibers in this area in such a manner to give the resulting embossment greater structural integrity. In effect a permanent crease or bend is imparted to the web at the edge of the embossment which results in greater embossment distinctness and a greater firmness retention for the embossed web.

Figure 6:
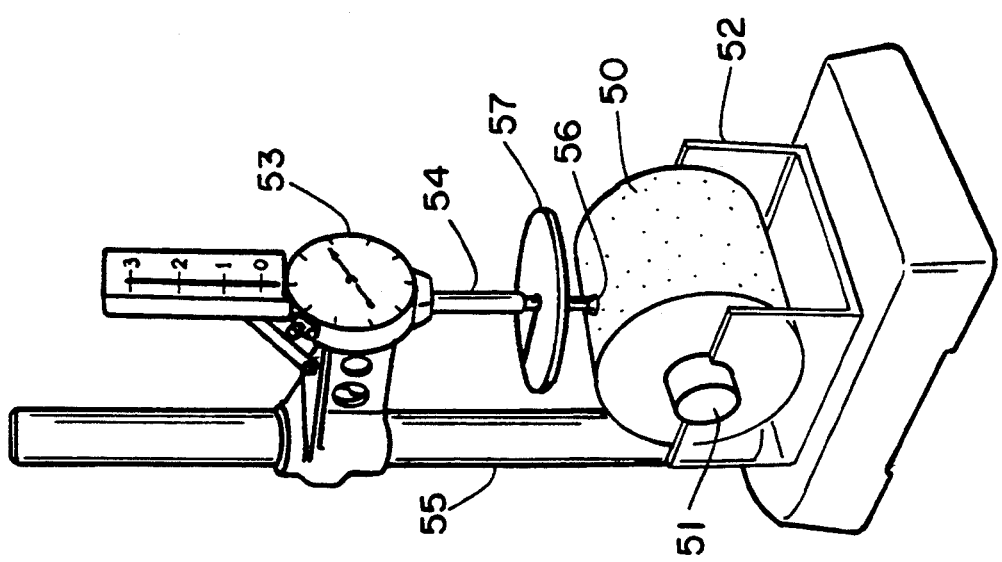
FIG. 6 is an illustration of the apparatus used to measure the Firmness Index for roll products such as bath tissue and paper towels.

FIG. 6 illustrates the apparatus used to measure the Firmness Index for roll products. The apparatus is available from B.C. Ames Company, Waltham, Mass. 02154 and is known as an Ames #16 Bench Comparator. Shown is a roll product 50 being measured which is supported on a core shaft 51, which in turn is supported by a suitable stand 52. A dial indicator 53 (#3223 long range indicator having a 3 inch range) mounted on the comparator stand displays the distance of travel of the probe rod 54 and displays readings from 0–100 in increments of 0.001. The length of the post 55 of the comparator stand is 15 inches long. The tip of the probe rod is fitted with a contact point 56 having a 13/64 inch diameter and a 11/64 inch radius of curvature (Model P-100 Ames contact point). The probe rod is adapted to be loaded with slotted weight discs 57 to vary the load and resulting travel of the probe rod in deflecting the surface of the product. The total downward force exerted by the probe rod when unloaded is between 70-80 grams.

When carrying out the Firmness Index procedure, the roll product is placed on the core shaft and holder so the indicator probe is approximately centered on the roll, end to end, and hits the apex of the roll curvature. The indicator probe is gently lowered onto the surface crown of the roll and the height of the dial indicator is adjusted until the reading on the dial indicator falls between 1.5 and 1.9 inches. The product roll is then rotated to a different center position and the dial indicator reading is recorded after the probe rod has been in contact with the product roll for 15 seconds. This is the first reading. Then, with one hand, the indicator probe is firmly grasped with the thumb and forefinger above the indicator dial using the dial housing for support. With the other hand, a 1 pound weight disc is placed on the indicator probe. The indicator probe is then gently lowered onto the sample roll surface. After the indicator probe has been in contact with the product roll for 15 seconds, the dial indicator reading is taken. This is the second reading. Subtract the second reading from the first reading. The difference is a measure of the roll firmness. Repeat the foregoing procedure at two random positions around the circumference of the product roll, each position being a fixed distance from each end of the roll. For bath tissue, the second and third readings should be one inch from the roll edges. For paper towels, the second and third readings should be two inches from the roll edges. The average of the three readings is the Firmness Index for the product.

Figure 7:
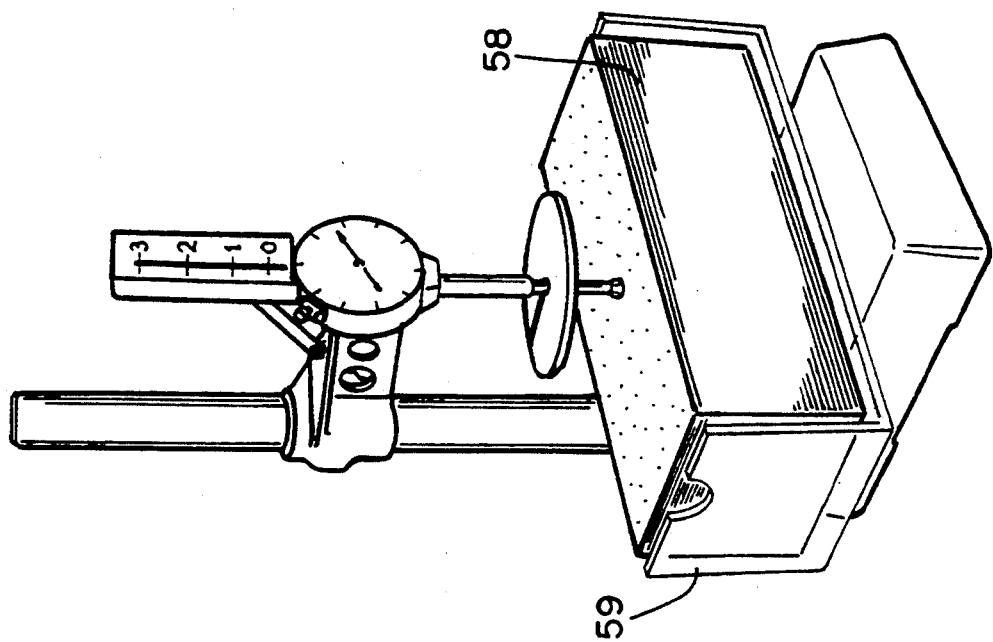
FIG. 7 is an illustration of essentially the same apparatus illustrated in FIG. 6, but modified slightly to measure the Firmness Index of stacked products such as facial tissue and table napkins.

FIG. 7 illustrates the apparatus used to measure the Firmness Index for products comprising a stack of webs 58, which is very similar to the apparatus described in regard to FIG. 6. The only difference from the apparatus illustrated in FIG. 6 is the elimination of the core shaft for supporting the product sample to be measured. Instead, for products comprising a stack of webs, the product stack is simply placed on a suitable tray support 59 or other suitable means which supports the corners of the stack and rests on base of the test apparatus. In most instances the probe rod will be long enough to reach the stack. If not, the product stack can be further supported by any suitable means which raises the stack sufficiently to be measured.

The procedure for determining the Firmness Index for a stack of webs is the same as that described above with regard to roll products, except that the three measurements to be averaged are taken at different locations. The first measurement is taken at the center of the product, as viewed from above. The second and third measurements are taken at diametrically opposite corners of the product, one inch from both edges which form the chosen corner. As before, the average of the three measurements is the Firmness Index for the product stack.

Figure 8A:
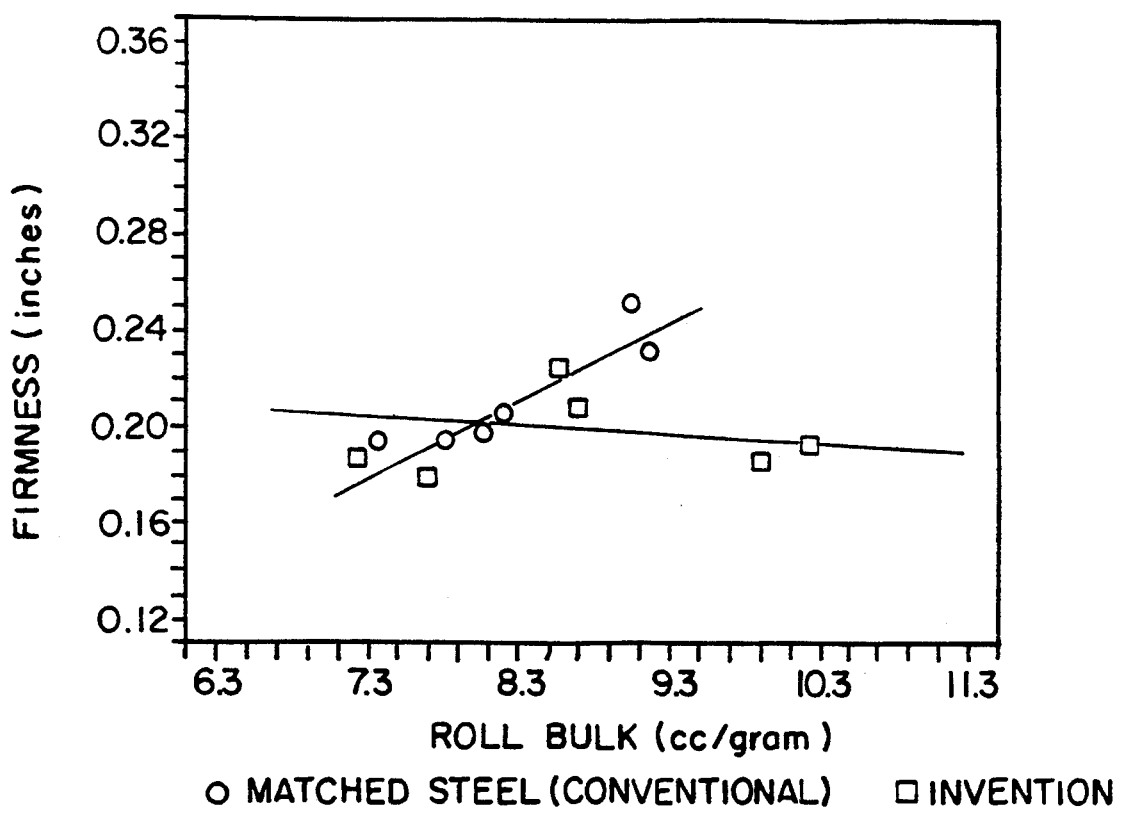
FIGS. 8A and 8B are plots of roll bulk vs. roll Firmness Index for embossed bath tissue of this invention compared to the same tissues embossed using matched steel rolls.
Figure 8B:
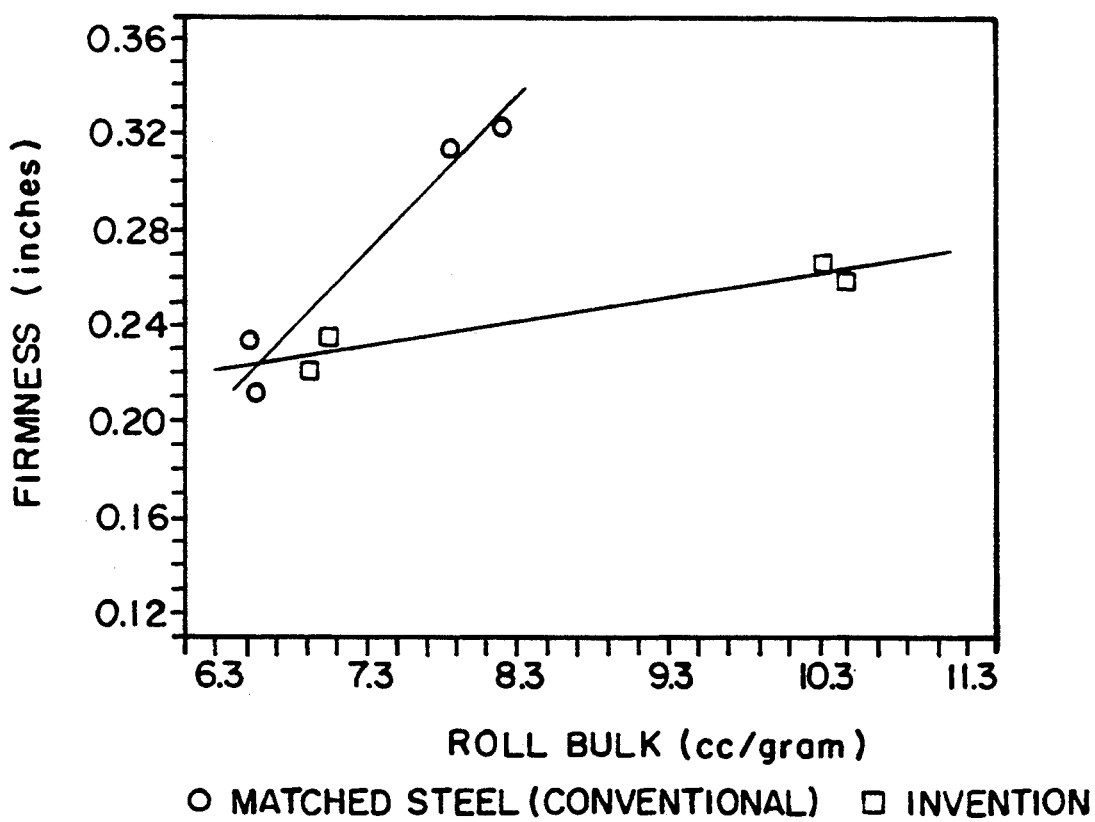

The relationship of roll Firmness Index and roll Bulk for two different embossed webs is illustrated in FIGS. 8A and 8B, in each case graphically illustrating a significant advantage of this invention compared to conventional embossing. The plot of FIG. 8A represents a comparison of a throughdried tissue web which was embossed by matched steel embossing rolls on the one hand and, on the other hand, by laser engraved rubber embossing rolls in accordance with this invention. The embossing pattern for both pairs of embossing rolls was the butterfly pattern illustrated in FIG. 9. The basesheet was a one ply, throughdried web having a basis weight of 33 grams per square meter and a geometric mean tensile strength of about 1300 grams per 3 inches of width. The furnish was a homogeneous mixture of 60 weight percent softwood bleached kraft and 40 weight percent hardwood bleached kraft papermaking fibers. The matched steel embossing roll elements appeared in cross-section as illustrated in FIG. 1 and had a depth of 0.042 inch, a base width of 0.067 inch, and an apex width of 0.025 inch. The laser engraved embossing roll elements appeared in cross-section as illustrated in FIG. 4 and had dimensions set forth in the description of FIG. 4. In each case, a 16 inch wide roll of the basesheet material was unwound, embossed at three different embossing levels, perforated every 4½ inches to define individual sheets, and wound onto a 1⅜ inch diameter core to form a log having a 300 sheet count. The log was then cut with a band saw into three product rolls of single-ply bath tissue. For the matched steel embossing, the three different levels of embossing were obtained by three different levels of engagement of the embossing elements: 0.015 inch, 0.020 inch, and 0.024 inch off bottom. For the laser engraved embossing, the three different levels of embossing were obtained by placing shims between the embossing roll bearing housings and increasing the spacing by 0.005 inch at a time. The initial setting was subjectively determined to give relatively heavy embossing. After the basesheet was embossed at all three conditions, the procedure was replicated to obtain two data points for each condition to improve the confidence level of the data. The results are plotted in FIG. 8A.

FIG. 8B is a similar plot, but for a different basesheet. The basesheet used for this plot was a wet pressed, two-ply tissue web having a combined basis weight of 31 grams per square meter and a geometric mean tensile strength of about 1100 grams. The furnish was a homogeneous blend of hardwood, softwood, bagasse and secondary papermaking fibers. The procedure and the embossing rolls were otherwise as described above with respect to FIG. 8A, except that only two levels of embossing element engagement were tested for the matched steel embossing: 0.016 inch and 0.013 inch. The laser engraved embossing rolls were adjusted once by 0.005 inch using shims as described above.

As is illustrated by both plots, as the Bulk is increased the Firmness Index increases for the matched steel product. (An increasing Firmness Index means decreasing firmness.) For the products of this invention, however, the Firmness Index remained relatively constant as the Bulk was increased. Hence by utilizing the method of this invention, one can increase roll Bulk while maintaining a desireable level of roll firmness. At the same time, a more distinct, well-defined embossing pattern is obtained.

It will be appreciated that the foregoing description and examples, given for purposes of illustration, are not to be construed as limiting the scope of this invention, which is intended to include all equivalents thereto.

We claim:

1. A method for embossing a web comprising deflecting the web between a plurality of engaging unmatched male and female embossing elements having sidewalls sloped at an angle to the plane of the undeflected web during embossing, wherein the sidewall slope of the female embossing elements is different than the sidewall slope of the male embossing elements with which the female embossing elements are engaged.

2. The method of claim 1 wherein the sidewall slope of the female embossing elements is less than the sidewall slope of the engaging male embossing elements.

3. The method of claim 1 wherein the sidewall slope of the female embossing elements is greater than the sidewall slope of the engaging male embossing elements.

4. The method of claims 1 or 2 or 3 wherein the sidewall slope of the male embossing elements is at least about 2° different than the sidewall slope of the female embossing elements.

5. The method of claims 1 or 2 or 3 wherein the sidewall slope of the male embossing elements is from about 5° to about 10° different than the sidewall slope of the female embossing elements.

6. The method of claims 1 or 2 or 3 wherein the sidewall slope of the male embossing elements is from about 50° to about 70°.

7. The method of claims 1 or 2 or 3 wherein the embossing elements are a deformable material.

8. The method of claims 1 or 2 or 3 wherein the embossing elements are rubber or plastic.

9. The method of claims 1 or 2 or 3 wherein the embossing elements are laser engraved.

10. The method of claims 1 or 2 or 3 wherein the web is a tissue web.

11. A method of embossing a tissue web comprising deflecting the tissue web between a plurality of engaging unmatched, laser-engraved, rubber or plastic male and female embossing elements having sidewalls sloped at an angle to the plane of the undeflected tissue web during embossing, wherein the sidewall slope of the female embossing elements is different than the sidewall slope of the male embossing elements with which the female embossing elements are engaged, and wherein the bulk of the tissue web is increased.

12. The method of claim 11 wherein the sidewall slope of the female embossing elements is less than the sidewall slope of the engaging male embossing elements.

13. The method of claim 11 wherein the sidewall slope of the female embossing elements is greater than the sidewall slope of the engaging male embossing elements.

* * * * *